United States Patent [19]

Olin et al.

[11] 4,246,788

[45] Jan. 27, 1981

[54] METHOD AND APPARATUS FOR SAMPLING OF A PARTICLE-BEARING GAS

[75] Inventors: John G. Olin, Carmel Valley, Calif.; Norman C. Ahlquist, Seattle, Wash.

[73] Assignee: Sierra Instruments, Inc., Carmel Valley, Calif.

[21] Appl. No.: 965,224

[22] Filed: Nov. 30, 1978

[51] Int. Cl.³ ............................................. G01N 1/22
[52] U.S. Cl. ............................................. 73/421.5 R
[58] Field of Search ............... 73/421.5 R, 421.5 A, 73/28

[56] References Cited

U.S. PATENT DOCUMENTS 3,965,748 6/1976 Boupel ..................... 73/421.5 A

FOREIGN PATENT DOCUMENTS 703079 1/1954 United Kingdom ............... 73/421.5 R
927271 of 1963 United Kingdom ............... 73/421.5 A
703079 1/1954 United Kingdom ............... 73/421.5 R

*Primary Examiner*—S. Clement Swisher
*Attorney, Agent, or Firm*—Thomas R. Berthold

[57] ABSTRACT

A method and apparatus for sampling a particle-bearing gas in which a vacuum is applied to the gas to generate a stream of gas, the flow of the stream is maintained constant, and particles are collected from the stream. A constant flow controller responsive to the static pressure of the gas in the stream provides a flow restriction which gradually decreases to compensate for a gradually increasing flow restriction caused by particles collecting on an initially particle-free collection filter located in the stream.

26 Claims, 3 Drawing Figures

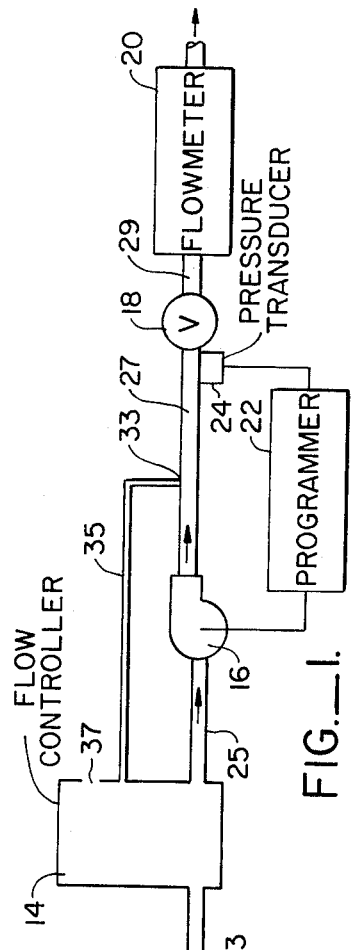
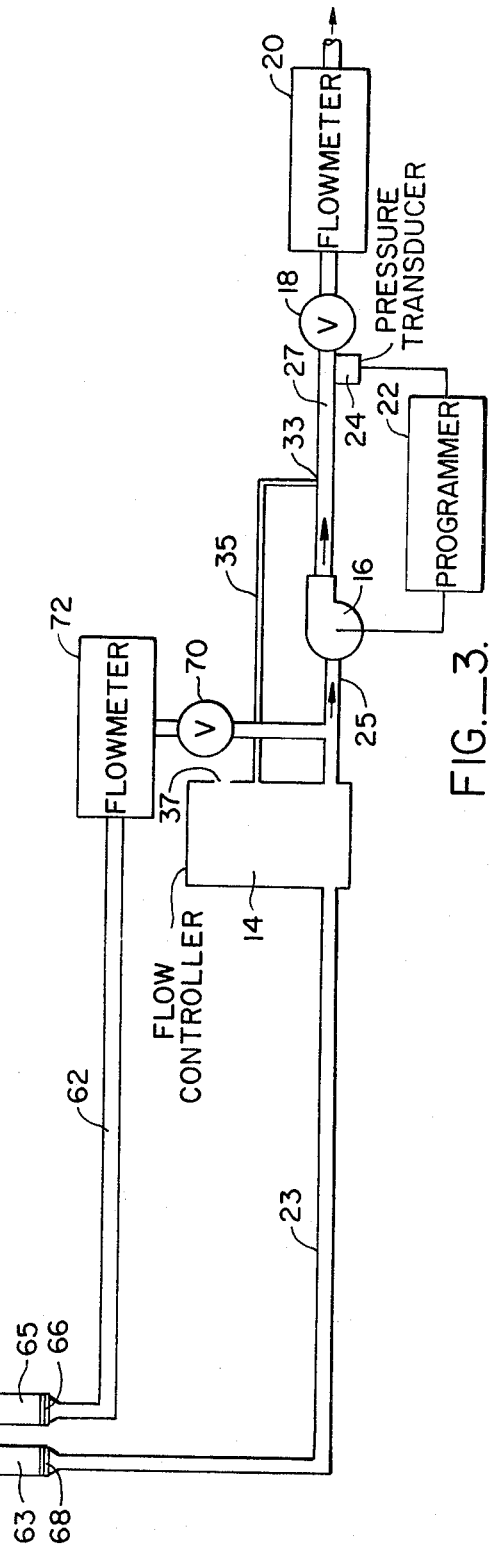
FIG._1.
FIG._3.

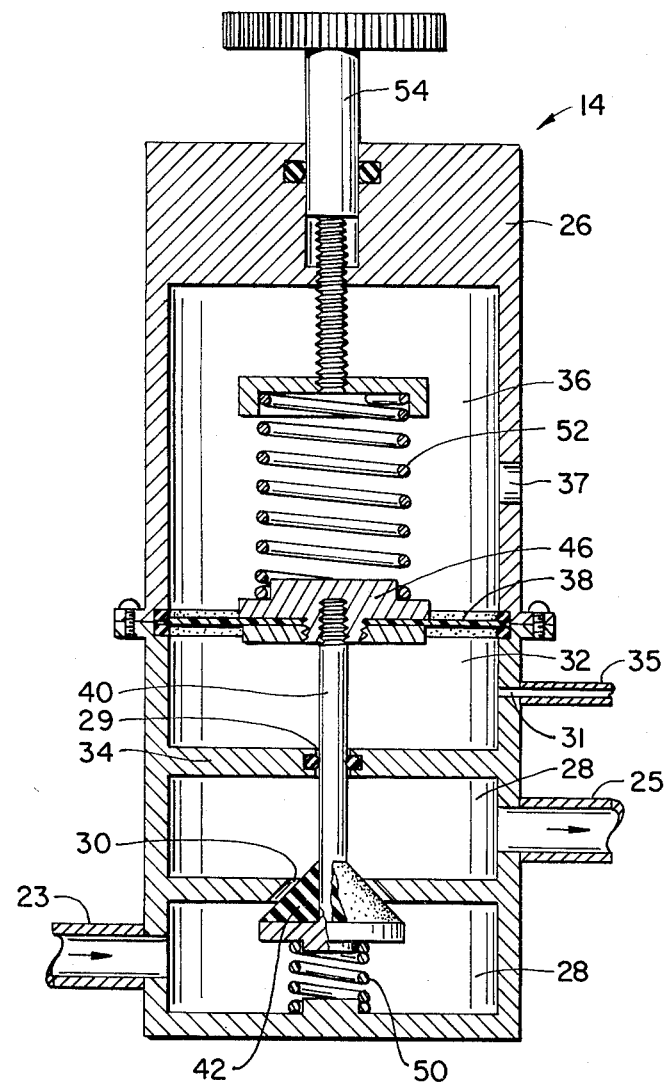
FIG._2.

METHOD AND APPARATUS FOR SAMPLING OF A PARTICLE-BEARING GAS

BACKGROUND OF THE INVENTION

This invention relates to a method and apparatus for the determination of particle concentration in a particle-bearing sample gas. More specifically, this invention relates to maintaining the rate of flow of the gas relatively constant during sampling so that the volume of gas sampled and therewith the concentration of particles in the gas can be more readily and accurately determined.

In conventional gas sampling devices, such as those used to determine the concentration of solid particulate matter suspended in air, a vacuum is applied to the sample gas so as to generate a flowing stream of gas. A filter of a specific pore size for filtering particles greater than a predetermined size collects particles from the flowing stream of gas. The filter is weighed before and after the sampling period so as to determine the total weight of particles greater than a predetermined size collected during the sampling period. Over a period of time, for example, a 24 hour sampling period, the flow rate past the filter decreases as particles collect on the filter. This flow rate reduction can be quite significant, for example up to 50% over a 24 hour period, when the particles being collected from the gas are substances, such as soot, which tend to clog the collection filter.

In order to determine the average number of particles per unit volume in the sample gas it is necessary to determine the total volume of gas which has passed through the collection filter. Because of the reduction in flow rate caused by the collection of particles on the filter, the conventional practice has been to compute the average flow rate of the gas from measured initial and final flow rates. Obviously such a computation is accurate only if the decrease in flow rate is linear with time.

A recent development in the area of particle-bearing gas sampling devices is the virtual impactor, a dichotomous gas sampler which divides the gas into two flow paths. The gas in the two paths flows at substantially different flow rates and bears particles of different sizes. With this recent development in which a single vacuum source applies a vacuum to the sample gas and the flow of the gas is divided into two paths, each path having its own filter for the collection of particles of a predetermined size, the accuracy of the conventional computational method to arrive at the total volume of gas sampled and thus the particle concentration of the different sized particles, becomes even more suspect.

It is apparent that the computation of particle concentration in a sample gas can be more readily and accurately determined if the flow rate of the stream of gas generated by the vacuum source can be maintained constant throughout the sampling period. One method of maintaining the flow rate of the stream of sample gas constant involves varying the speed of the vacuum source, i.e., the vacuum pump, in response to the mass flow rate sensed proximate the collection filter by a flow rate transducer. As particles collect on the filter and the flow rate decreases, the pump speed must increase to increase the flow rate. Such a method is complex and has proven to have a high failure rate, with a resultant increase in manpower and servicing costs.

In an alternative method, generally used in only high volume gas samplers, a flow regulator sensitive to the dynamic pressure of the relatively high velocity gas, maintains the flow rate constant. The flow regulator comprises a movable circular disk located in the stream between the filter and the pump and having its working surface oriented normal to the direction of the flowing gas. The disk is restrained by a spring which is compressed by the dynamic pressure of the flowing gas acting on the working surface of the disk. The disk is thus movable longitudinally within the conduit confining the stream. The portion of the conduit surrounding the disk has a generally conical shape which converges in a downstream direction so that the area of the annular opening defined by the outer periphery of the disk and the inner wall of the conical portion of the conduit varies with the longitudinal position of the disk in the conduit. Thus as particles collect on the filter and the flow rate decreases, the corresponding decrease in dynamic pressure allows the compressed spring to move the disk away from the converging portion of the conduit, thereby increasing the annular opening and the flow rate.

This alternative method of flow rate control is dependent upon the dynamic pressure of the flowing gas and is thus limited to high volume gas sampling. Additionally, because the dynamic pressure opposing the compressive spring varies with the square of the velocity of the gas and because the spring force is linear only over a relatively small compression, the flow rate is maintained constant only over a small range of flow rates, thereby preventing constant flow rate control during long sampling periods in which substantial flow rate reduction is typical.

While the present invention is generally directed to a method and apparatus for sampling a static body of gas, U.S. Pat. Nos. 2,982,131; 3,859,842; and 3,965,747 disclose methods for sampling a moving body of gas, such as exhaust gases in a flue, in which the sample gas flows through the sampling device at generally the same velocity that it is flowing in the flue, thus permitting the sampling to be conducted isokinetically.

SUMMARY OF THE INVENTION

The present invention provides a method and apparatus for maintaining the flow rate of a stream of gas constant throughout long duration sampling periods. The invention permits the accurate determination of particle concentration in a sample gas over the wide range of flow rates at which the gas may possibly be sampled. The vacuum pump which generates the stream of gas operates at its optimum design capacity, consumes a minimum of energy, generates minimal heat throughout the entire sampling period, and operates at a minimum noise level.

The invention provides a particle-bearing gas sampling device which maintains the flow rate of a stream of gas relatively constant throughout the sampling period, and comprises generally a vacuum source for generating a stream of gas, a filter for collecting particles from the stream, a flow rate selector located downstream of the pump for selecting the desired flow rate, and throttling means located between the vacuum source and the filter for varying the flow into the vacuum source in response to the static pressure sensed in the stream. Additionally, a programmer electrically coupled to the vacuum source and to a flow sensing or pressure sensing transducer located downstream of the vacuum source initiates sampling at a predetermined time, and terminates vacuum application at the end of a predetermined sampling period and also in the event the flow rate falls below a predetermined value. Means are also provided for maintaining constant flow rate with a virtual impactor in which the sample gas is divided into two paths, the gas in the two paths flowing at substantially different flow rates and bearing particles of different sizes.

The throttling means for varying the flow into the vacuum source in response to the static pressure of the flowing gas stream is a modified pressure regulator and comprises generally a multi-chambered housing and a movable plunger located within the housing. The flowing stream of gas passes through the first chamber and through an orifice within the first chamber. The movable plunger, which is responsive to the difference between the ambient pressure of the sample gas and the static pressure in the flowing gas stream, has a lower conically shaped portion positioned in the orifice. The upper portion of the plunger is connected to a generally flexible diaphragm which separates the second and third chambers and which provides a fluid seal between them. The second chamber of the housing is fluidly connected to the stream, preferably downstream of the vacuum source. Thus, the pressure in the second chamber is the static pressure of the gas in the stream downstream of the vacuum source, i.e., on the compressor side of the vacuum pump. The third chamber is open to the ambient atmosphere, typically the atmosphere of the gas being sampled. Both the upper and lower ends of the plunger are operatively connected to respective ends of the housing by compressive springs.

At the initiation of gas sampling, the programmer turns on the vacuum pump and begins timing the sampling period. The flow rate selector, e.g., a valve, located downstream of the vacuum source, is varied until the desired flow rate is reached. The vacuum pump acts on the static body of sample gas to generate a flowing stream of gas which flows through the collection filter, through the first chamber and the orifice of the throttling means, through the pump and valve and out to the atmosphere. As particles begin to collect on the collection filter the flow rate upstream of the vacuum source decreases. Correspondingly the static pressure in the stream downstream of the pump and thus the pressure in chamber two of the throttling means decreases. Since the ambient pressure of the static body of gas being sampled remains relatively constant, a pressure differential between the second and third chambers forces the diaphragm and thus the plunger downward so as to increase the annular opening defined by the conical plunger portion positioned in the orifice. This increased opening at the orifice relaxes the flow restriction at the orifice and compensates for the increased flow restriction at the collection filter. Accordingly, the flow rate is maintained relatively constant.

In the event of a surge in line voltage to the vacuum pump, which would tend to increase the pump speed and thus the flow rate of the stream, the static pressure sensed in the stream downstream of the vacuum source increases. In such an instance, the pressure differential between the second and third chambers of the throttling means moves the diaphragm and the plunger upward so as to decrease the annular opening at the orifice. The result is a decrease in flow rate despite the increased pump speed, thereby maintaining the flow rate of the stream relatively constant.

If for some reason the flow rate of the stream falls below a predetermined low value, a flow sensing or pressure sensing transducer located proximate the vacuum source signals the programmer to terminate vacuum application and the gas sampling device is automatically shut off.

After a predetermined time period measured by the programmer the programmer terminates vacuum application and the sampling process is completed. The collection filters which were weighed before sampling began are weighed again to determine the weight of specific sized particles collected by the respective filters.

The gas sampling device includes means for adapting its use with a dichotomous sampler, such as a virtual impactor, which divides the sample gas into two paths having different flow rates. Generally speaking, a flow restrictor having an opening of fixed area is placed in the path having the reduced flow rate. This flow restrictor effectively chokes the flow of gas in the reduced flow rate path so as to maintain the flow rate in that path relatively constant regardless of the increasing flow restriction caused by particles collecting on the filter in that path. The gas flowing in the two paths is recombined downstream of the collection filters and upstream of the vacuum source.

Since the flow rate of the stream of gas is maintained relatively constant during the sampling period and since the sampling period is accurately timed by the programmer, the total volume of gas sampled from the static body of sample gas is accurately determined. Thus the ultimate computation of the concentration of particles of a specific size in the sample gas is more readily and accurately determined.

The novel features which are believed to be characteristic of the invention, together with objects and advantages thereof, will be better understood from the following description considered in connection with the accompanying drawings in which preferred embodiments of the invention are illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a block diagram of the gas sampling device.

FIG. 2 is a sectional view of the constant flow controller of the gas sampling device.

FIG. 3 is a block diagram of the gas sampling device adapted for use with a dichotomous sampler.

DESCRIPTION OF THE PREFERRED EMBODIMENTS

The gas sampling device is illustrated in FIG. 1 and permits the accurate determination of particle concentration in the sample gas by generating a flowing stream of the gas at a relatively constant flow rate and for a predetermined time period. Generally speaking, the gas sampling device comprises in series an inlet 10 for the gas to pass from the static body of sample gas, a particle collection means, such as filter 12, for collecting particles suspended in the gas, a constant flow controller 14, a vacuum source, such as vacuum pump 16, a flow rate selector, such as valve 18, means for measuring the flow rate, such as flowmeter 20, and interconnecting conduits 23, 25, 27, 29. Also provided with the gas sampling device is a programmer 22 electrically coupled to pump 16 and to a pressure sensing transducer 24 for controlling the application of vacuum to the sample gas. The programmer 22 includes means, e.g. suitable timing circuitry, for automatically initiating and terminating vacuum application to the sample gas so that sampling may be conducted at preselected intervals and for a predetermined period.

The constant flow controller 14, more fully depicted in FIG. 2, throttles the flow of the stream of gas upstream of pump 16 so that the gas flows at a relatively constant flow rate during the sampling period. The constant flow controller 14 comprises generally a multi-chambered housing 26 and a movable plunger 40 located therein. Housing 26 is operatively connected to the gas sampling device so that the stream of flowing gas passes through the lower chamber 28 in housing 26 during its passage from inlet 10 to pump 16. Located within chamber 28 is an orifice 30 through which the flowing stream of gas must pass during its passage through chamber 28. Lower chamber 28 is sealed from middle chamber 32 by means of a rigid plate 34 having an opening 29 therein. Middle chamber 32 is in turn separated and fluidly sealed from upper chamber 36 by a generally flexible diaphragm 38.

Secured to diaphragm 38 and projecting through opening 29 in plate 34 is a movable plunger 40. Plunger 40 has a lower portion 42 which hsa a generally conical configuration and which is positioned in the center of orifice 30 in chamber 28. Both lower portion 42 and upper portion 46 of plunger 40 are operatively connected to respective ends of housing 26 by springs 50 and 52. Springs 50 and 52 and flexible diaphragm 38 permit the longitudinal movement of plunger 40 within housing 26. The longitudinal movement of plunger 40 varies the position of conically shaped lower portion 42 within orifice 30 in chamber 28, thereby varying the area of the generally annular shaped opening defined in orifice 30 by conically shaped portion 42 of plunger 40.

Middle chamber 32 of housing 26 is in fluid communication with the stream of gas, preferably at a point 33 downstream of vacuum pump 16, by means of opening 31 in chamber 32 and hose 35. Thus the pressure in middle chamber 32 is generally the static pressure of the gas in the stream at the point of fluid communication with the stream, such as depicted as point 33 on conduit 27.

Upper chamber 36 of housing 26 of the constant flow controller 14 is open to the ambient atmosphere by means of opening 37. Thus the pressure in chamber 36 is the pressure of the static body of sample gas if the gas sampling device is surrounded by the sample gas.

A screw member 54 is connected to spring 52 and thus to upper portion 46 of plunger 40 for adjusting the equilibrium position of plunger 40 in housing 26.

The invention can be better understood by considering the function of the component parts during operation. Prior to the initiation of gas sampling, screw member 54 is ajusted so that lower portion 42 of plunger 40 is positioned within orifice 30 in a manner that the annular opening thereby defined provides a restriction to flow greater than the flow restriction provided by the initially particle-free filter 12.

The initiation of sampling is begun by programmer 22 which turns on pump 16 and begins timing the sampling period. The pump 16 applies a vacuum to the static body of sample gas and generates a stream of flowing gas which flows into inlet 10, through initially particle-free filter 12, through conduit 23, chamber 28 of constant flow controller 14, conduit 25, and into pump 16. The stream of gas ultimately passes out pump 16, conduit 27, valve 18, and flowmeter 20, after which it exhausts to the ambient atmosphere. The valve 18, which is a variable flow restriction in the stream, is varied to select the desired flow rate of the stream of sample gas. The selection of the flow rate is facilitated by flowmeter 20 which displays the flow rate as valve 18 is adjusted. Once valve 18 is adjusted so that the desired flow rate has been reached, the sampling period has begun.

As the stream of particle-bearing gas generated by pump 16 passes through filter 12, particles are collected on filter 12. As particles continue to collect on filter 12, the restriction flow at filter 12 gradually increases and the flow rate of the stream gradually decreases. The gradual reduction in flow rate in this manner, in the absence of other factors, causes a corresponding reduction in the static pressure of the gas downstream of the vacuum source, and thus the pressure in middle chamber 32 decreases with increasing flow restriction at filter 12. While the pressure in chamber 32 decreases corresponding to increasing flow restriction at filter 12, the ambient pressure and thus the pressure in chamber 36 of constant flow controller 14 remains relatively constant. Thus, the pressure differential across diaphragm 38 between chambers 36 and 32 of constant flow controller 14 changes. This changing pressure differential decreases the force acting on diaphragm 38 from the pressure in chamber 32. Plunger 40 is moved away from its initial equilibrium position by the force of spring 52 and thus is moved downward. The downward movement of plunger 40, and specifically of conically shaped lower portion 42 of plunger 40, increases the annular opening defined in orifice 30 by conically shaped lower portion 42 of plunger 40, thereby relaxing or decreasing flow restriction at orifice 30. The continued increase in flow restriction by particles collecting on filter 12 is thus automatically and immediately compensated by a decrease in flow restriction at orifice 30, thereby maintaining flow rate throughout the system relatively constant. Thus, despite continued collection of particles on filter 12 during sampling and the corresponding reduction in flow rate at filter 12, pump 16 operates at constant speed and at its optimum design capacity throughout the entire sampling period.

After the gas sampling device has been operating for the predetermined time period, a timer in programmer 22 terminates vacuum application to the sample gas by shutting off pump 16. The total volume of gas sampled during this sampling period is thus readily and accurately determined from a knowledge of the volumetric flow rate, which was maintained constant, and the duration of the sampling period. The accurate determination of the total volume of gas sampled facilitates the determination of the mass of particles per unit volume in the sample gas. The filter which was weighed before sampling began is weighed again to determine the total weight of particles collected.

If for some reason, e.g. abnormally rapid clogging of filer 12, the flow decreases below the limit of controllability, transducer 24, which is preferrably a pressure transducer or alternatively a flow transducer signals programmer 22 to shut off vacuum pump 16. Any conventional circuitry, e.g. a relay or suitable solid state equivalent, in programmer 22 will perform this desired function.

Referring now to FIG. 3, means are provided for adapting the gas sampling device so as to maintain constant flow control in a dichotomous sampler, such as virtual impactor 60, which directs the sample gas into two paths.

Virtual impactor 60 comprises an inlet 61 for the passage of the sample gas and for the various sized particles suspended in the sample gas, two outlets 63, 65 connected respectively to conduits 23, 62, and two filters 68, 66 located proximate respective outlets 63, 65. Conduit 23 connected to outlet 63 is part of the gas sampling device described above. Conduit 62 is in fluid communication with conduit 25 of the above-described gas sampling device between constant flow controller 14 and pump 16. Located between outlet 65 and conduit 25 and in fluid communication with conduit 62 are a a flowmeter 72 and a flow restrictor 70. Conduits 23 and 62 confine the gas to flow in two paths.

The gas flowing in the two paths flows at substantially different flow rates and bears particles of different sizes. In the embodiment depicted in FIG. 3, the "coarse" particles, i.e. those larger than the particle size cut-point of virtual impactor 60, pass through outlet 65 and are borne by gas flowing in the path confined by conduit 62 at a flow rate that is less than the flow rate of the gas flowing in conduit 23. The coarse particles pass from inlet 61 to outlet 65 because of their greater momentum. The "fine" particles, i.e. those smaller than the particle size cut-point of virtual impactor 60, have a lesser momentum and are directed from inlet 61 into outlet 63 by gas flowing at a flow rate greater, e.g., by a factor of 10, than the flow rate of the gas in conduit 62. The fine particles are collected on filter 68. Generally speaking, in such a virtual impactor, all of the coarse particles from inlet 61 pass through outlet 65 and are collected on filter 66. However, some of the fine particles, the exact amount being proportional to the flow rates in the respective paths, also pass from inlet 61 through outlet 65 and are collected on filter 66.

The gas which has been diverted into two paths by virtual impactor 60 is recombined downstream of filters 66, 68 and upstream of pump 16. The flow restrictor 70 located in the path confined by conduit 62 is an adjustable valve which allows preselecting the desired flow rate. The preselected flow rate is monitored by flowmeter 72. The flow through flow restrictor 70 is choked because of the relatively small area of the opening provided by flow restrictor 70 and because the pressure in conduit 25 upstream of vacuum pump 16 is substantially less than atmospheric. Since the flow rate through filter 66 is relatively small, e.g. one-tenth that through filter 68, clogging of filter 66 is not a problem, the flow through conduit 62 remains relatively constant and the flow through flow restrictor 70 remains choked.

In the operation of the gas sampling device with virtual impactor 60, fine particles collect on filter 68 and the flow rate in conduit 23 gradually decreases. Constant flow controller 14 compensates for this gradual increase in flow restriction by decreasing the flow restriction at orifice 30 in the manner as above described. Despite the flow rate compensation provided by constant flow controller 14, the flow rate in the outlet 65 and conduit 62, i.e., the reduced flow rate path, remains constant. Thus, throughout the entire sampling period the total flow rate is maintained relatively constant despite the increasing flow resistance provided by particles collecting on filters 68, 66. Since the flow rate in the path in which gas bearing the coarse particles is flowing, i.e., conduit 65, is also maintained relatively constant because of the choked condition provided by flow restrictor 70, the flow rate in the path in which gas bearing the fine particles is flowing, i.e. outlet 63, must also be maintained constant.

At the termination of the sampling period, which occurs in the manner as above described for the gas sampler shown in FIG. 1, the two filters 68, 66, which were weighed before sampling, are again weighed to determine the total weight of particles collected on each of them. A correction to the weight of filter 66 is made for the portion of fine particles which have been collected on filter 66. This correction may be accurately made because the weight of fine particles collected on filter 66 is directly related to the flow rates in the respective paths. Thus the maintainance of constant total flow rate, as well as constant flow rate in each of the paths, facilitates the ultimate determination of the concentration of particles of a specific size when a dichotomous sampler is used.

As should now be apparent, the present invention provides a method and apparatus for the rapid and accurate determination of particle concentration in a particle-bearing sample gas. The determination of particle concentration is facilitated by maintenance of constant flow rate during the sampling period. Because constant flow rate is maintained by sensing the static pressure of the flowing stream of gas as particles gradually collect on the collection filter and thereby gradually decrease the flow rate, the gas sampling device is capable of maintaining constant flow rate during both high and low volume gas sampling. Additionally, the sensing of the static pressure downstream of the vacuum pump so as to throttle the flow rate upstream of the vacuum pump permits the pump to operate at a constant speed and at its optimum design capacity, thereby minimizing energy consumption, eliminating the addition of heat energy to the stream, and minimizing the noise level.

When used with a dichotomous sampler, the present invention permits the accurate determination of the concentration of various sized particles suspended in a sample gas by maintaining the flow rate in the two paths of the dichotomous sampler constant despite the fact that particles are collecting on the filters in both paths.

While the preferred embodiments of the present invention have been illustrated in detail, it should be apparent that modifications and adaptations of those embodiments will occur to those skilled in the art. However, it is to be expressly understood that such modifications and adaptations are within the sphere and scope of the present invention as set forth in the following claims.

What is claimed is:

1. A method of sampling a relatively static body of particle-bearing ambient gas for the determination of particle concentration, the gas being sampled by a device of the type utilizing a vacuum pump, the method comprising the steps of:
generating a stream of flowing gas from the ambient gas to be sampled by operating the vacuum pump;
continuously collecting particles in said stream and retaining the collected particles within said stream, such that the rate of flow of said stream and therewith the static pressure in said stream tends to decrease;
continuously sensing the static pressure in said stream; and
continuously throttling the flow of said stream upstream of the vacuum pump in response to the difference between said sensed pressure and the ambient pressure of the gas while maintaining the speed of the vacuum pump relatively constant, whereby the rate of flow of said stream is maintained relatively constant.

2. A method according to claim 1 including the step of preselecting the rate of flow of said stream.

3. A method according to claim 1 including the step of, prior to collecting particles from said stream, sorting the particles into groups according to size.

4. A method according to claim 1 including the step of terminating said vacuum application when the rate of flow of said stream reaches a predetermined value.

5. The method according to claim 1 including the steps of timing the duration of said vacuum application and terminating said vacuum application when said timed duration reaches a predetermined value.

6. The method according to claim 1 wherein the step of collecting includes the step of filtering said stream.

7. In a method of determining particle concentration in a gas wherein a flowing stream of gas is generated by a vacuum source and particles are collected from the stream, an improved method of maintaining the volumetric flow rate of the stream relatively constant so as to facilitate the determination of particle concentration, the improvement comprising the steps of:
sensing the static pressure of the stream of gas downstream of the vacuum source; and
regulating the pressure of the stream upstream of the vacuum source in response to said sensed pressure downstream, whereby the static pressure downstream of the vacuum source and therewith the volumetric flow rate of the stream is maintained relatively constant so as to facilitate the determination of particle concentration in the gas.

8. The method according to claim 7 including the step of comparing said sensed pressure to the ambient pressure of the gas.

9. The method according to claim 7 wherein the step of regulating the pressure upstream includes the step of varying the flow upstream.

10. The method according to claim 7 wherein the step of regulating the pressure upstream includes the steps of increasing the pressure in the stream upstream of the vacuum source in response to a decrease in said sensed pressure downstream and decreasing the pressure in the stream upstream of the vacuum source in response to an increase in said sensed pressure downstream.

11. The method according to claim 7 including the step of preselecting the volumetric flow rate of the stream.

12. The method according to claim 7 including the step of measuring the volumetric flow rate of the stream and terminating vacuum application to the gas when said measured volumetric flow rate reaches a pre-determined value.

13. The method according to claim 7 including the steps of timing the duration of vacuum application and terminating vacuum application when said timed duration reaches a pre-determined value.

14. In a method of determining the concentration of particles in a sample gas, the method being of the type wherein a vacuum is applied to the sample gas so as to generate a flowing stream of gas and wherein particles are collected on a filter located in the stream of flowing gas, an improved method of maintaining the volumetric rate of flow of the stream relatively constant as particles collect on an initially particle-free filter in the stream and tend to reduce the volumetric rate of flow of the stream, the improvement comprising the steps of:
preselecting the volumetric rate of flow of the stream;
restricting the flow of the stream at a point between the filter and the vacuum source, so that the flow restriction at said restriction point is greater than the flow restriction provided by an initially particle-free filter;
continuously sensing the static pressure of the stream downstream of the vacuum source; and
relaxing the restriction to flow at said restriction point in response to a decrease in said sensed pressure downstream so that the flow restriction at said restriction point decreases in response to the decrease in said sensed pressure downstream, whereby the volumetric rate of flow of the stream is maintained generally at said preselected rate as particles are collected on an initially particle-free filter in the stream and the flow restriction at the filter gradually increases.

15. An apparatus for the determination of particle concentration in a particle-bearing sample gas, the apparatus comprising in combination:
means for applying a vacuum to the sample gas so as to generate a flowing stream of gas;
inlet means in fluid communication with the sample gas and said vacuum application means;
means for collecting particles from the flowing stream, said particle collecting means being in fluid communication with and located between said inlet and said vacuum application means;
means located between said particle collecting means and said vacuum application means for regulating the pressure in the stream, said pressure regulating means further comprising a housing having an orifice therein through which the stream passes and means movable within said orifice and responsive to the difference between the static pressure in the stream and the ambient pressure of the sample gas for varying the opening at said orifice; and
conduit means interconnecting said inlet, said particle collecting means, said pressure regulating means, and said vacuum application means for confining the stream.

16. Apparatus according to claim 15 including means for selecting the volumetric rate of flow of the stream, said flow rate selecting means being in fluid communication with and located downstream of said vacuum application means.

17. Apparatus according to claim 15 including means for measuring the volumetric rate of flow of the stream.

18. Apparatus according to claim 15 including a second particle collecting means in fluid communication with said inlet and said vacuum application means; second conduit means interconnecting said inlet, said second particle collecting means and said vacuum application means; a flow restrictor located in said second conduit means between said second particle collecting means and said vacuum application means for maintaining the rate of flow of gas through said second particle collecting means relatively constant and less than the volumetric rate of flow of gas through said first particle collecting means.

19. Apparatus according to claim 15 including means coupled to said vacuum application means and responsive to pressure for terminating the application of vacuum to the sample gas and therewith the flow of the stream when the pressure reaches a pre-determined level.

20. Apparatus according to claim 15 including means coupled to said vacuum application means and responsive to the rate of flow of the stream for terminating the flow of the stream.

21. Apparatus according to claim 15 including timing means electrically coupled to said vacuum application means for terminating the application of vacuum to the sample gas at the end of a pre-determined time period.

22. For use in a particle-bearing gas sampling device of the type having a vacuum pump for generating a stream of flowing gas, an inlet for the sample gas, a filter located between the gas inlet and the vacuum pump for collecting particles from the stream of gas, and conduit means interconnecting the gas inlet, the filter, and the vacuum pump, an apparatus for maintaining the flow rate of the stream relatively constant as particles collecting on the filter tend to reduce the flow rate of the stream, said apparatus comprising:

means in fluid communication with the stream between the filter and the vacuum source for regulating the pressure of the stream, said pressure regulating means having an orifice therein for the passage of the stream and means movable within said orifice and responsive to the difference between the static pressure in the stream and the ambient pressure of the sample gas for varying the opening at said orifice and therewith the pressure in the stream; and means operatively connected to said pressure regulating means for sensing the static pressure of the stream.

23. An apparatus for the dichotomous sampling at a generally constant volumetric flow rate of a particle-bearing gas, the apparatus comprising in combination:

a vacuum pump for generating a stream of flowing gas;

a flow rate selector valve in fluid communication with said pump for selecting the volumetric flow rate of said stream;

a virtual impactor in fluid communication with the sample gas and said pump for dividing the sample gas into two paths;

a first filter located in said first path, and in fluid communication with said virtual impactor and said pump for collecting particles from the gas flowing in said first path;

a second filter located in said second path and in fluid communication with said virtual impactor and said pump for collecting particles from the gas flowing in said second path;

a flow restrictor located in said second path and in fluid communication with said second filter and said pump for maintaining the flow rate of gas in said second path relatively constant and less than the flow rate of gas in said first path;

means upstream of said pump for combining the gas flowing in said two paths into said stream; and a pressure regulator in fluid communication with and located between said said first filter and said pump, said pressure regulator further comprising means for sensing the static pressure of the gas in said stream, a chamber through which the gas flows from said first filter to said pump, said chamber having an orifice therein, and means responsive to the difference in pressure between the ambient pressure of the sample gas and said sensed static pressure for varying the opening at said orifice and therewith the rate of flow of said stream, whereby as particles collected on said first filter tend to reduce the flow rate of the gas flowing in said first path and therewith the sensed static pressure, the opening at said orifice is increased so as to maintain the volumetric flow rate of said stream generally at the rate selected by said flow rate selector.

24. Apparatus according to claim 23 including means coupled to said pump and responsive to the flow rate of said stream for terminating the flow of said stream.

25. Apparatus according to claim 23 including control means coupled to said pump for terminating the flow of said stream at the end of a predetermined time interval.

26. A method of sampling a particle-bearing gas for the determination of particle concentration, the gas being sampled by a device of the type haing a vacuum source, the method comprising the steps of:

applying a vacuum to the gas to be sampled so as to generate a stream of flowing gas;

collecting particles from said stream;

sensing the static pressure in said stream downstream of the vacuum source; and throttling the flow of said stream upstream of the vacuum source in response to said sensed pressure, whereby the rate of flow of said stream is maintained relatively constant.

* * * * *